United States Patent [19]
Kawaguri et al.

[11] Patent Number: 5,171,689
[45] Date of Patent: Dec. 15, 1992

[54] SOLID STATE BIO-SENSOR

[75] Inventors: Mariko Kawaguri, Suita; Shiro Nankai; Takashi Iijima, both of Hirakata, all of Japan

[73] Assignee: Matsushita Electric Industrial Co., Ltd., Osaka, Japan

[21] Appl. No.: 339,698

[22] Filed: Apr. 18, 1989

Related U.S. Application Data

[63] Continuation-in-part of Ser. No. 932,945, Nov. 28, 1986, abandoned, which is a continuation of Ser. No. 673,751, Nov. 8, 1984, abandoned.

[51] Int. Cl.⁵ ............... C12M 1/38; G01N 27/26
[52] U.S. Cl. ................. 435/290; 435/288; 435/817; 204/403; 128/635
[58] Field of Search ........... 128/635; 435/817, 287, 435/288, 290; 204/403

[56] References Cited

U.S. PATENT DOCUMENTS

| | | | |
|---|---|---|---|
| 3,791,988 | 2/1974 | Josef et al. | 252/408.1 |
| 4,024,042 | 5/1977 | Enfors et al. | 435/817 |
| 4,224,125 | 9/1980 | Nakamura et al. | 435/817 |
| 4,240,438 | 12/1980 | Updike et al. | 128/635 |
| 4,388,166 | 6/1983 | Suzuki et al. | 435/817 |
| 4,431,004 | 2/1984 | Bessman et al. | 128/635 |
| 4,450,842 | 5/1984 | Zick et al. | 128/635 |
| 4,458,686 | 7/1984 | Clark | 128/635 |
| 4,467,811 | 8/1984 | Clark | 128/635 |

OTHER PUBLICATIONS

Webster, Medical Instrumentation, Houghton Mifflin Co. (1978), see p. 540 FIG. 10.13.

Primary Examiner—David L. Lacey
Assistant Examiner—William K. Y. Chan
Attorney, Agent, or Firm—Birch, Stewart, Kolasch & Birch

[57] ABSTRACT

As the conventional simple bio-sensors for measuring the particular component in living bodies, there are those in which a change in dye caused by enzyme reaction is detected optically, but such bio-sensors had a problem that precision is low owing to disturbance of the color of liquid samples. With bio-sensors using an enzyme electrode, the precision was high, but operation of measurement was troublesome. The present invention made it possible to detect the concentration of the particular component electromechanically with rapidity, simplicity and high precision by merely putting a porous substrate containing at least enzyme on the electrode system and impregnating the body with a liquid sample.

17 Claims, 3 Drawing Sheets

SOLID STATE BIO-SENSOR

CROSS-REFERENCE TO RELATED APPLICATION

This application is a continuation-in-part of application Ser. No. 932,945 filed Nov. 28, 1986, now abandoned, which is a continuation of application Ser. No. 673,751, filed Nov. 8, 1984, now abandoned.

TECHNICAL FIELD

The present invention relates to a bio-sensor which makes it possible to determine the particular component of various biological samples with ease, rapidity and high precision.

BACKGROUND OF THE INVENTION

In recent years, various kinds of bio-sensor based on the specific catalytic action of enzyme have been developed, and particularly, their application to clinical inspection field is being tried. At the present day wherein inspection items and the number of specimens are increasing, bio-sensors which enable rapid and high-precision measurement are demanded.

A case of glucose sensor will be taken as example. In these days of remarkable increase of diabetes, for measurement and control of blood sugar in blood, there is a demand for sensors applicable to tests on whole blood, because it takes a very long time to centrifuge blood and measure the separated plasma as conventionally carried out. There is provided a simple sensor like the test paper used for urinalysis, and this sensor comprises a stick-form support and a carrier put on the support containing an enzyme which will react with glucose only and a dye which will change itself on enzyme reaction or by the product of the reaction. Blood is added to the carrier, and a change in the dye after a definite period of time is measured visually or optically. But, the measurement is largely disturbed by dyes in blood, so that its precision is low.

The multi-layer analytical carrier was thus proposed as shown in FIG. 1 (Japanese Utility Model Opening (KOKAI) No. 178495/1979). This carrier has a laminated structure wherein a reagent layer 2, developing layer 3, water-proof layer 4 and filter layer 5 are placed one upon another in this order on a transparent support 1. When a blood sample is dropped down to the carrier, the blood is first freed from its solid components such as red blood cells, blood platelets, etc. on the filter layer 5, uniformly diffuses into the developing layer 3 through small pores in the water-proof layer 4 and comes into reaction in the reagent layer 2. After completion of the reaction, light is passed through the transparent support in the direction of an arrow to measure the substrate concentration spectroanalytically. Although this carrier is complicated in structure as compared with the conventional sample stick-form carrier, an improvement in precision was attained by removing blood cells, etc. But, it takes a long time for the penetration and reaction of blood, so that there was a necessity to put the water-proof layer 4 for preventing the sample from drying and to incubate at high temperatures for accelerating the reaction, which caused a problem of the apparatus and carrier becoming complicated.

Thus, an electrode method comprising combining enzyme reaction with electrode reaction was developed as a simple method of good precision. Since there is no disturbance of colored substances in the electrode method, the liquid sample can be used as it is without a necessity for pre-treatment, and therefore, the measurement became simple and precision was also improved. A case of glucose sensor will be taken as example. A flow-type sensor was developed as shown in FIG. 2 in which a liquid sample, e.g. blood or urine, is added to the sensor while applying a definite voltage to a glucose oxidase immobilized electrode 6 and passing a buffer solution 7 through a conduit 8 made of insulating materials such as acrylic resin; glucose in the sample reacts with the immobilized glucose oxidase to produce hydrogen peroxide which is then oxidized at the electrode 6 to generate a current; and the glucose concentration of the sample can be detected by measuring the strength of the current. The sensor of this type enables as many specimens as 200 to 300 per hour to be measured with rapidity and high precision, but it had a problem that the apparatus becomes large in size. The so-called batch-type sensor as shown in FIG. 3 was thus developed in which a glucose oxidase immobilized electrode 11 is placed in a vessel 10 which is then filled with a buffer solution 12, and a liquid sample is added to the solution while stirring with a stirrer. The size of apparatus could be made fairly small by using this type, but there occurred problems that a stirrer is essential, and that foaming and turbulent flow are caused by stirring to exert an adverse effect on the precision. Also, there was a necessity to exchange the buffer solution and sometimes wash the electrode, and besides, because of the liquid sample being diluted with the buffer solution, precision was required for the amounts of buffer solution and liquid sample.

Thus, for simple measurement, a dry measurement-form sensor requiring no stirring apparatus is demanded, and besides a high precision is required.

DISCLOSURE OF THE INVENTION

The bio-sensor of the present invention is composed of an insulating plate and an electrode system comprising a working electrode and a counter electrode put thereon, said system being covered with a porous plate comprising at least one layer containing oxidoreductase. This sensor is intended to measure the concentration of substrates, e.g. urine sugar and blood sugar, by electrochemically detecting a reduced electron acceptor produced when it is impregnated with a liquid sample to carry out enzyme reaction, and also it is intended to measure the glucose concentration of fruit juices.

By using the bio-sensor of the present invention, measurement can be carried out by merely adding a liquid sample directly to the porous plate containing at least enzyme without using a buffer solution. Also, since the sample need not be diluted, there is no necessity to determine the sample and besides a trace amount of the particular component of the sample can be measured with simplicity and high sensitivity.

BEST FORM FOR PRACTICE OF THE INVENTION

Example 1

Figure 1:
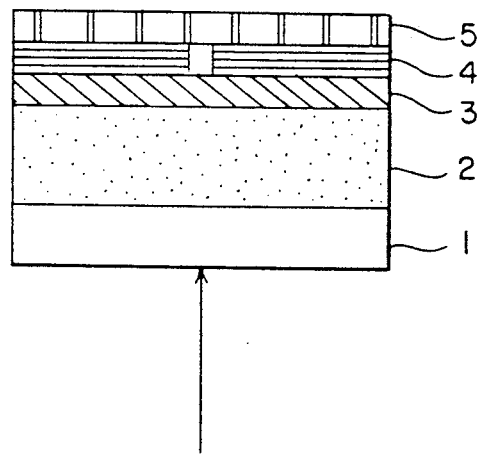
FIG. 1 is a typical view illustrating one embodiment of the conventionally used glucose sensors.
Figure 2:
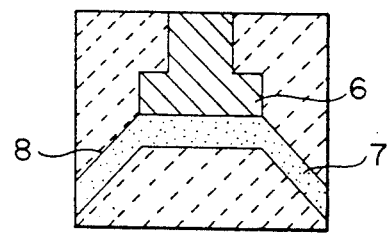
FIGS. 2 and 3 are typical views illustrating the conventional glucose sensor using an immobilized enzyme electrode.
Figure 3:
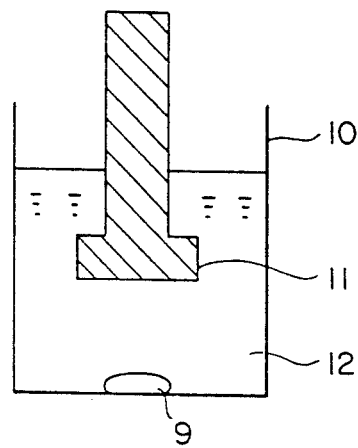
Figure 4:
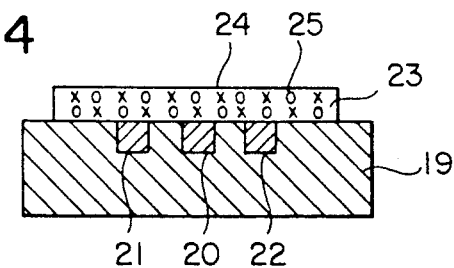
FIG. 4 is a typical view illustrating one embodiment of the bio-sensor of the present invention.

Explanation will be given on a glucose sensor which is one of bio-sensors. Glucose oxidase was used as oxidoreductase, and potassium ferricyanide was used as an oxidizing dye working in conjugation with the oxidoreductase. FIG. 4 is a typical view illustrating one embodiment of a glucose sensor. Pieces of platinum wire of 1 mm in diameter were buried in an insulating plate 19 made of a polyvinyl chloride resin to prepare a working electrode 20, counter electrode 21 and reference electrode 22, and nylon non-woven fabric 23 was put on the foregoing electrode system so as to cover the system. This nylon non-woven fabric 23 was prepared as follows: 100 mg of glucose oxidase and 150 mg of potassium ferricyanide are dissolved in 1 c.c. of a phosphate buffer solution (pH 5.6), and nylon non-woven fabric is impregnated with the solution thus prepared and dried at room temperature.

A standard glucose solution, a liquid sample, was added to the nylon non-woven fabric 23 and after allowing the solution to well penetrate into the fabric, voltage was applied to the working electrode 20 with the reference electrode 22 as standard and varied at a rate of 0.1 V/sec so that it drew a saw-toothed line between 0 V and +0.5 V. For example, when the glucose in a sample is oxidized by glucose oxidase 24 carried on a nylon non-woven fabric 23, potassium ferricyanide 25 is reduced by enzyme/dye conjugation reaction to produce potassium ferrocyanide. On oxidizing the potassium ferrocyanide by sweeping voltage applied to the working electrode 20, anodic current flows. This anodic current is directly proportional to the amount of dye changed, and when the dye is present in sufficient amounts, since said amount corresponds to the substrate concentration, the concentration of glucose, a substrate, can be detected by measuring the strength of the anodic current. The relationship between the strength of peak current obtained and the concentration of glucose added showed a very good rectilinearity in the range of up to 500 mg/dl as shown by A in FIG. 5. The nylon non-woven fabric 23 was exchanged at every measurement, but reproducibility was good. Also, the amount of the standard glucose solution added was varied from 20 μl to 140 μl, but a definite value was obtained independently of the amount of the solution as shown by C and D in FIG. 6 when the glucose concentration was definite.

Example 2

Figure 5:
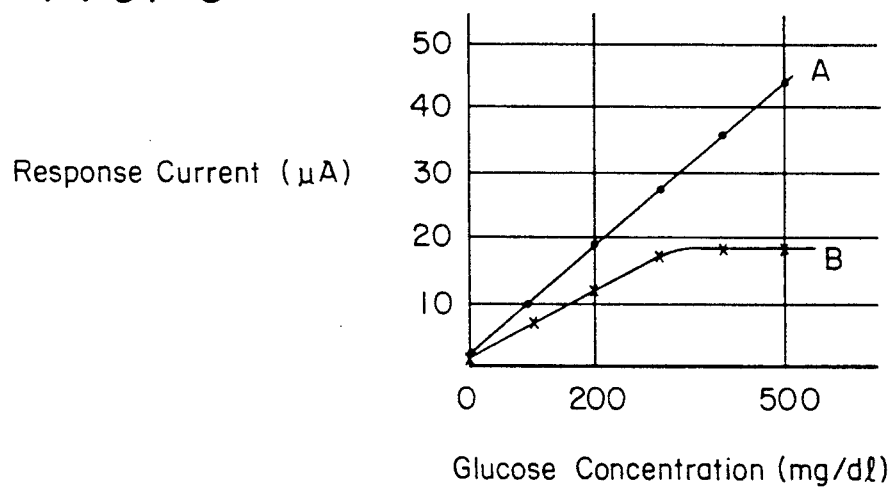
FIGS. 5 and 6 show the response characteristics of the bio-sensor shown in FIG. 4.
Figure 6:
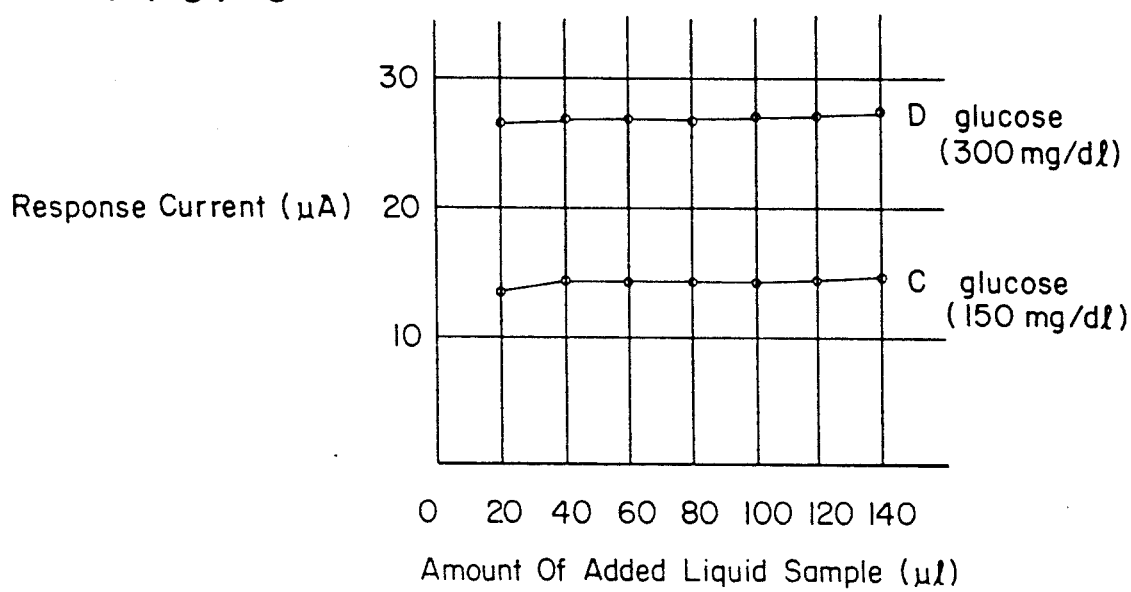

The electrode system used in Example 1 was covered at the upper surface with nylon non-woven fabric carrying glucose oxidase only, and then measurement was carried out in the same manner as in Example 1 with dropwise addition of the standard glucose solution. In this system, oxygen contained in air and the liquid sample is used as the electron acceptor; when glucose reacts with glucose oxidase, hydrogen peroxide is produced in an amount corresponding to the glucose concentration and oxidized at the surface of the electrode; and the strength of anodic current generated by the oxidation is measured to obtain the glucose concentration. The peak of the current obtained, as shown by B in FIG. 5, showed a rectilinear rise up to 300 mg/dl but little or no rise at higher concentrations than this. The reason for this may be considered to be due to that supply of oxygen is not sufficient when the substrate concentration is high. But, measurement was possible at low concentrations of the substrate.

Example 3

Figure 7:
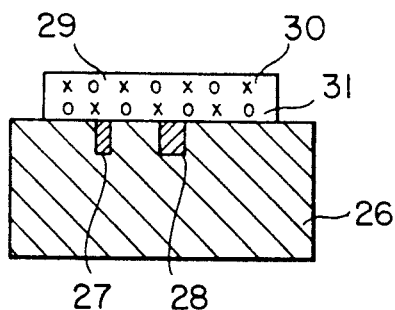
FIGS. 7, 8 and 9 are typical views illustrating other embodiments of the bio-sensor of the present invention.

FIG. 7 is a typical view illustrating another embodiment of the glucose sensor of the present invention. As shown in Example 1, measurement can stably be carried out if a three-electrode system comprising a working electrode, a counter electrode and a reference electrode is used, but it can also be carried out with a two-electrode system comprising a working electrode and a counter electrode. Platinum was buried in an insulating plate 26 made of a polyvinyl chloride resin to prepare a working electrode 27 and counter electrode 28. To stabilize the potential, the area of the counter electrode 28 was made at least more than two times as large as that of the working electrode 27. In the same manner as in Example 1, this electrode system was covered at the upper surface with nylon non-woven fabric 29 carrying glucose oxidase 30 and potassium ferricyanide 31, and measurement was carried out with dropwise addition of the standard glucose solution. It was found that the reproducibility was slightly poorer than in Example 1, but that glucose concentrations of up to 500 mg/dl could be measured. A silver/silver chloride (Ag/AgCl) counter electrode was used in place of the platinum one 28, and it was found that the potential was stabilized, and that measurement could be carried out with good reproducibility if the area of this electrode was made equal to that of the electrode 27.

Example 4

Figure 8:
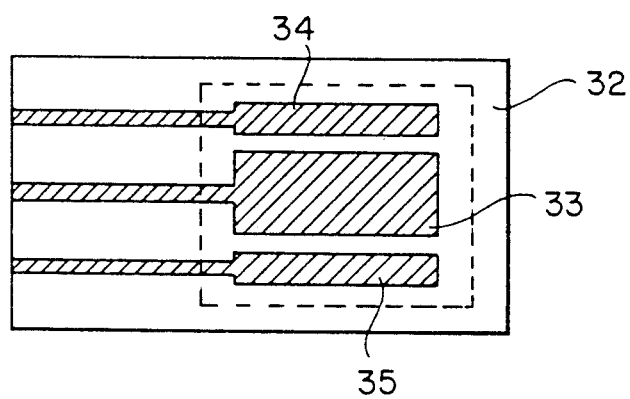

FIG. 8 is a sensor comprising an insulating plate 32 made of a polyvinyl chloride resin and a working electrode 33, counter electrode 34 and reference electrode 35 in a thin film form which were produced from platinum on the plate by the spattering method. On these electrodes was placed the same nylon non-woven fabric carrying the enzyme and oxidizing dye as used in Example 1 so as to cover the region shown by a dotted line. Thereafter, response to the standard glucose solution was measured in the same manner as in Example 1 to obtain the same good response as in the electrode system in FIG. 4. Next, measurement was repeated using the standard glucose solution of the same concentration as well as the electrodes and nylon non-woven fabric newly exchanged at every measurement, and as a result, a very good reproducibility was obtained. Consequently, if the electrodes are produced by the spattering method or vacuum deposition method as in this example, electrodes having the same response characteristics and any desired shape can be produced in large amounts, and by covering the electrodes with a porous plate carrying enzyme and oxidizing dye, high-performance bio-sensors which can be disposed after use, can be provided.

Example 5

Figure 9:
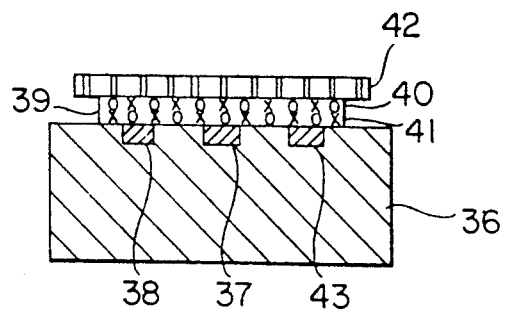

FIG. 9 is a typical view illustrating one embodiment of a glucose sensor. Platinum is buried in an insulating plate 36 made of a polyvinyl chloride resin to prepare a working electrode 37, counter electrode 38 and reference electrode 43. Nylon non-woven fabric 39 is placed on the electrode system comprising these electrodes so as to cover the system. This nylon non-woven fabric 39 is a one prepared through the same dissolution, impregnation and drying as in Example 1, and it carries glucose oxidase 40 (oxidoreductase) and potassium ferricyanide 41 (oxidizing dye), which works in conjugation with oxidoreductase, in a dry form. On the upper surface of the fabric 39 is placed a filter layer 42 comprising porous polycarbonate (pore diameter, 1 μm).

On adding blood (whole blood) to this sensor, large molecules in blood such as red blood cells were filtered off on the filter layer 42, and glucose in the blood came into reaction at the reaction layer comprising the nylon non-woven fabric 39 in the same manner as in Example 1, whereby the glucose concentration could be detected at the electrode system. That is, from the strength of a current obtained, the glucose concentration could be detected based on a calibration curve previously prepared with a standard glucose solution. The current strength and glucose concentration showed a good correlation as compared with the conventionally used types of glucose sensor. The reaction layer comprising the enzyme and oxidizing dye and the filter layer were exchanged at every measurement, but the reproducibility was good in either sample of standard glucose solution and blood. Also, the amount of blood added was varied from 20 μl to 140 μl, but the amount of glucose showed a definite value independently of said amount since the dye and enzyme were present in sufficient amounts.

By using the porous of polycarbonate as the filter layer 42, blood cells and viscous substances present in blood could previously be removed, and as a result, stains on the electrode could be decreased. Without the filter layer, blood cells adhered to the electrode during a long-term use to lower the strength of current obtained, so that there was necessity to wash the electrode with alcohol. But, by using the filter layer, it became possible to maintain the response with good reproducibility by merely washing the electrode with water. Also, it was found that the porous plate which was useful to the above object was a one having a pore diameter within about 3 μm. Further when the porous substrate of polycarbonate was used after dipped in a 1% aqueous solution of surface active agent, e.g. polyethylene glycol alkylphenyl ether (trade name: Triton X) and dried, filtration of blood became very fast with a further improved reproducibility. Hitherto, there was a problem that, since blood is fairly viscous, its filtration rate is low. But, by using a filter layer previously treated with surface active agents, filtration became fast and also reaction with enzyme and dye proceeded rapidly and uniformly to come to an end in as short a time as only about one minute after addition of a test sample. When the surface active agent was not used, it took about 1.5 minutes for the reaction to come to an end after addition of blood, and therefore the effect of the surface active agent to accelerate the measurement was large.

As the surface active agent, polyoxyethylene glycerin fatty acid esters, polyoxyethylene alkyl ethers, polyethylene glycol fatty acid esters and the like can be used in addition to the foregoing example. By previous treatment of not only the filter layer but also the dye and enzyme with the surface active agent, the rates of filtration and penetration became fast to make it possible to accelerate the measurement.

The reaction layer comprising the oxidizing dye and enzyme is preferably a hydrophilic porous membrane so that it can absorb the liquid sample rapidly to advance the enzyme reaction. For example, when filter paper, non-woven fabric of pulp, porous plate of ceramic or glass, etc. were used in addition to the nylon non-woven fabric, penetration of the liquid sample was quick and uniform, and reproducibility was also good. Further, the rate of penetration of the sample into the above porous membrane was larger in the membrane pretreated with the foregoing surface active agent than in the untreated membrane. The filter layer having an effect to accelerate the measurement may be placed on the electrode or the upper surface of the reaction layer. Penetration of the liquid sample was fastest when the filter layer was placed below the reaction layer, and the reaction time was also short. While, when the filter layer was placed on the reaction layer, there was an advantage that the reaction proceeds smoothly and a high precision is obtained because the solid component of blood can first be filtered off so that there is no disturbance of blood cells, etc. in the reaction layer. For the filter layer, use of non-woven fabrics, chemical fibers, paper (filter paper), etc. was thought of. But, the material component of blood cells could completely be filtered off by using membrane filter having a pore diameter of less than about 2–3 μm. Also, filtration could be carried out stepwise by laminating the membrane filter layer with the foregoing non-woven fabric, chemical fiber, paper or the like.

In the above sensor, various methods could be employed to carry glucose oxidase (enzyme) and potassium ferricyanide (dye). For example, it was also possible to laminate two pieces of nylon non-woven fabric carrying the enzyme and dye, respectively. In carrying potassium ferricyanide on nylon non-woven fabric 39, potassium ferricyanide crystals on the fabric became much finer and more soluble in liquids by hot air-drying nylon non-woven fabric impregnated with a potassium ferricyanide solution than by drying the fabric at room temperature. The potassium ferricyanide crystal on the fabric became further finer when the nylon non-woven fabric impregnated with a potassium ferricyanide solution was dipped in an organic solvent having a great solubility in water, for example ethanol, and vacuum-dried. By carrying potassium ferricyanide in a finely pulverized form, even a highly viscous sample such as blood completed the reaction within one minute with an improved reproducibility. Since the enzyme is poorly resistant to heat, etc., it was dried at room temperature after dipped in the above organic solvent. Also, when both the enzyme and oxidizing dye are carried on one piece of porous plate, the dye and enzyme could be carried in a very soluble form by dipping the porous plate carrying a color and an enzyme ethanol and vacuum-drying. Further, the enzyme may be immobilized by crosslinking with glutaraldehyde after dipping, and it could be stored stably for a long time by such immobilization.

Example 6

In Example 5, a porous membrane such as nylon non-woven fabric was used as a porous substrate, but in addition to this, inorganic carriers such as $SiO_2$ also may be used in the form of a porous plate produced by press-molding. When $SiO_2$ was pressure-molded into a size of 7 mm (diameter)×1 mm (thickness) by 5 t/cm$^2$ pressure, impregnated with an aqueous solution containing glucose oxidase and potassium ferricyanide and then dried, penetration of blood into this molded $SiO_2$ was a little slower than in the nylon non-woven fabric. Since, however, the porous membrane of polycarbonate also can be produced at the same time by pressure-molding, the filter layer and reaction layer could integrally be molded to simplify their production. Further, it was also possible to finely pulverize glucose oxidase and potassium ferricyanide and after mixing and adding a small amount of $SiO_2$, to pressure-mold the mixture. In this case, since the glucose oxidase and potassium ferricyanide rapidly dissolve in blood to form a uniform mixture, the reaction became very fast.

Example 7

In Example 5, blood was filtered using a filter layer treated with a surface active agent. In this example, however, this treated filter layer was further impregnated with 10 mg/c.c. of a sodium fluoride (anticoagulant) solution and dried, and the procedure of Example 5 was repeated but using the filter layer thus obtained. As a result, blood could be filtered in only ten seconds without coagulation, and besides measurement was completed in as short a time as only 50 seconds after addition of blood. Thus, this method made a great contribution to acceleration of measurement.

As the anticoagulant, sodium fluoride is suitable because it is stable and simple in handling. But, heparin, sodium citrate, ethylenediamine tetraacetic acid, etc. were also useful to carry out blood filtration rapidly.

As the dye, potassium ferricyanide used in the foregoing examples is suitable because it reacts stably, but p-benzoquinone is suitable for acceleration because it is fast in reaction rate. Further, 2,6-dichlorophenolindophenol, methylene blue, phenazine methosulfate, potassium β-naphthoquinone-4-sulfonate, etc. may also be used.

The sensors in the foregoing examples can be applied to not only glucose but also systems in which oxidoreductase takes part such as alcohol sensors, cholesterol sensors and the like. Glucose oxidase was used as the oxidoreductase, but other enzymes such as alcohol oxidase, xanthine oxidase, cholesterol oxidase, etc. may also be used.

Possibility of Application to Industry

The bio-sensor of the present invention makes it possible to measure the particular component in various biological samples with rapidity, high precision and simplicity, so that its utility value in clinical inspection is very large.

The porous plate fixed on the insulating substrate plate has a pore size which is effective for retaining a liquid sample of body fluids such as blood, urine, saliva, lympha, sweat, tears and the like and other liquid samples such as wine, fruit juices or glucose solution. Moreover, any biological sample containing a specific substrate to be measured may be fixed on the porous plate so long as the porous plate has a pore size effective for retaining the sample. Preferably, the pore size of the plate is between 1000 Angstroms and 1 mm.

The bio-sensor of the present invention is applicable to various fields such as biologicals, foods, industrials, etc. Further, the bio-sensor can be used for determining alcohol concentration, cholesterol concentration, etc. other than glucose concentration in a liquid phase. One of ordinary skill in the art can readily understand that the glucose content or cholesterol content in lympha, for instance, can be determined according the invention. Examples of food or industrial fields include fruit juices or glucose solution, but similar liquid biological materials can be determined in a similar manner. For instance, the alcohol concentration in wine may be determined by using an alcohol oxidase (alcohol sensor) instead of a glucose oxidase.

What is claimed is:

1. A bio-sensor for measuring a substrate concentration of a liquid sample, comprising:
   at least a working electrode and a counter electrode,
   an insulating substrate plate which supports and insulates the working electrode and the counter electrode from one another, and
   a porous plate fixed on the insulating substrate plate, wherein said porous plate carries at least an oxidoreductase and a buffer, the oxidoreductase and the buffer are in a dry state, and wherein the bio-sensor is constructed so as not to contain a liquid containing chamber.

2. The bio-sensor according to claim 1, wherein the buffer is a phosphate.

3. The bio-sensor according to claim 1, wherein an electron acceptor is carried on the porous substrate in a dry state.

4. The bio-sensor according to claim 1 further comprises an oxidizing dye.

5. The bio-sensor according to claim 4, wherein the oxidizing dye is a member selected from the group consisting of potassium ferricyanide, p-benzoquinone, 2,6-dichlorophenolindophenol, methylene blue, phenazine methosulfate and potassium beta-naphtoquinone-4-sulfonate.

6. The bio-sensor according to claim 1, wherein the oxidoreductase is a member selected from the group consisting of glucose oxidase, alcohol oxidase, xanthine oxidase and cholesterol oxidase.

7. The bio-sensor according to claim 1, wherein the oxidoreductase is glucose oxidase.

8. The bio-sensor according to claim 1, wherein the working electrode comprises platinum.

9. The bio-sensor according to claim 8, wherein the porous plate has a pore diameter of less than 3 micron meters.

10. The bio-sensor according to claim 1, further comprises a reference electrode.

11. The bio-sensor according to claim 1, wherein the porous plate is a hydrophilic porous membrane.

12. The bio-sensor according to claim 1, further comprising a filter having a pore size of less than 3 micron meters positioned and arranged on the porous plate.

13. The bio-sensor according to claim 12, wherein an anticoagulant is carried on the filter.

14. The bio-sensor according to claim 12, which further comprises a reference electrode.

15. The bio-sensor according to claim 1, wherein the counter electrode comprises platinum or silver/silver chloride.

16. The bio-sensor according to claim 1, wherein the pore size of the porous plate is between 1000 Angstroms and 1 mm.

17. A bio-sensor for measuring a substrate concentration of a liquid sample, which comprises:
   at least a working electrode and a counter electrode,
   an insulating substrate plate which supports and insulates the working electrode and the counter electrode from one another, and
   a porous plate fixed on the insulating substrate plate, wherein said porous plate carries at least an oxidoreductase and a buffer, the oxidoreductase and the buffer are in a dry state and contacts the electrodes without an intervening electrolyte layer between (i) the oxidoreductase and the buffer and (ii) the electrodes, and wherein the bio-sensor is constructed so as not to contain a liquid containing chamber.

* * * * *